US010092434B2

United States Patent
Neely

(10) Patent No.: US 10,092,434 B2
(45) Date of Patent: Oct. 9, 2018

(54) TENDON SUPPORTING BAND

(71) Applicant: Lorenzo Neely, Ypsilanti, MI (US)

(72) Inventor: Lorenzo Neely, Ypsilanti, MI (US)

(*) Notice: Subject to any disclaimer, the term of this patent is extended or adjusted under 35 U.S.C. 154(b) by 0 days.

(21) Appl. No.: 14/158,200

(22) Filed: Jan. 17, 2014

(65) Prior Publication Data

US 2014/0135670 A1    May 15, 2014

Related U.S. Application Data

(60) Provisional application No. 61/958,908, filed on Aug. 9, 2013.

(51) Int. Cl.
*A61F 5/00* (2006.01)
*A61F 13/00* (2006.01)
*A61F 5/01* (2006.01)

(52) U.S. Cl.
CPC ................... *A61F 5/0102* (2013.01)

(58) Field of Classification Search
CPC .... A61F 13/00; A61F 13/0123; A61F 13/061; A61F 13/14; A61F 13/08; A61F 5/0111; A61F 5/0123
USPC .......... 606/207, 201–204; D24/169, 64, 190; 602/26, 5, 20–23, 60–64; 2/311, 312, 2/161.1–161.8, 159, 167, 239, 162, 160; 128/878
See application file for complete search history.

(56) References Cited

U.S. PATENT DOCUMENTS 3,283,894 A * 11/1966 Hafner et al. ................ 206/306
3,942,525 A    3/1976 Dragan
4,019,734 A *  4/1977 Lee ..................... A63B 21/0552
                                                  482/125
4,334,528 A *  6/1982 Gauvry .......................... 602/26
4,466,428 A    8/1984 McCoy
4,777,946 A   10/1988 Watanabe
4,805,620 A    2/1989 Meistrell
5,304,202 A *  4/1994 Stahl ................. A61B 17/1322
                                                  606/201

(Continued)

FOREIGN PATENT DOCUMENTS

GB            235628 A *  6/1925 ......... A61B 17/1327

OTHER PUBLICATIONS

Medi-Dyne Healthcare Products, Cho-Pat(r) Tennis Elbow Splint, found at http://www.cho-pat.com/products/tenniselbowsplint.php, found on Sep. 17, 2013.

*Primary Examiner* — Kim M Lewis
(74) *Attorney, Agent, or Firm* — Wayne State Patent Clinic

(57) ABSTRACT

A tendon strap for engaging adjacent a joint of a user including a flexible tubular member (10) of a length with first and second ends (12, 14) sufficient to completely encircle the joint of the user at a point immediately adjacent to the joint with sufficient additional length to allow for adjustment. A buckle (16) connected adjacent the first end (12) of the tubular member (10). The buckle (16) for adjustably receiving the second end (14) of the tubular member (10) in interlocking relationship to secure the tendon strap to the joint. A fastener (18) and a securing member (22) for securing the tubular member (10) to the buckle (16) with the first and second ends (12, 14) inserted through the buckle (16). The first and second ends (12, 14) reversibly folded over a central portion of the tubular member (10) to encircle opposite sides of the buckle (16).

18 Claims, 2 Drawing Sheets

(56) References Cited

U.S. PATENT DOCUMENTS

| | | | | |
|---|---|---|---|---|
| 5,607,448 A | * | 3/1997 | Stahl | A61B 17/1322 606/201 |
| 5,848,981 A | * | 12/1998 | Herbranson | A61F 7/10 601/134 |
| 6,077,242 A | | 6/2000 | Falk | |
| 6,080,124 A | | 6/2000 | Falk | |
| 6,361,549 B1 | * | 3/2002 | Asatourian | A61F 5/30 606/204 |
| 6,463,637 B1 | * | 10/2002 | Carnahan | 24/578.15 |
| 6,485,448 B2 | * | 11/2002 | Lamping et al. | 602/26 |
| 2012/0101329 A1 | * | 4/2012 | Dela Cruz | A61F 5/41 600/39 |

* cited by examiner

TENDON SUPPORTING BAND

CROSS-REFERENCE TO RELATED APPLICATIONS

This application claims priority of U.S. Provisional Patent Application Ser. No. 61/958,908, filed Aug. 9, 2013, the entire disclosure of which is hereby expressly incorporated by reference herein.

FIELD OF THE INVENTION

The invention relates to an orthopedic bandage having an adjustable method of securing a band adjacent to a user's joint to put compressive pressure on the associated tendon to properly align the tendon, relieve discomfort in the tendon as a result of joint usage, or otherwise provide therapeutic effect when used.

BACKGROUND

Tendon straps are widely known in the prior art. These known tendon straps suffer from various disadvantages, including: the straps lose tension during use; are uncomfortable to wear; and are bulky to wear. The tension problem associated with conventional tendon straps has been previously addressed by using hook and loop fasteners, such as VELCRO®, using a buckle to secure a strap-like member, or including a tendon supporting member as part of a larger joint brace. The hook and loop fasteners are disadvantageous because hook and loop fasteners do not adequately prevent the strap from losing tension during use. Using a buckle to secure a strap suffers the disadvantage of discomfort resulting from the use of a strap from compression and often requires an additional piece of material to prevent the contact of the buckle with a user's skin during use. Configurations that include a tendon supporting member as part of a larger joint brace create unnecessary bulk making the larger joint brace undesirable to be used in an athletic setting. For examples of various configurations of known tendon supporting devices see the devices disclosed in U.S. Pat. No. 4,334,528; U.S. Pat. No. 6,077,242; U.S. Pat. No. 6,080,124; U.S. Pat. No. 4,466,428; U.S. Pat. No. 4,777,946; U.S. Pat. No. 3,942,525; and U.S. Pat. No. 4,805,620. While each of these devices appears suitable for its intended purpose, the configurations disclosed are generally uncomfortable or bulky to wear, less than satisfactory in operation, or both. The problem with hook and loop secured tendon supporting devices is that the hook and loop connection tends to lose tension during use, resulting in a reduction in therapeutic effected gained from securing the device. Other configurations will use straps that have a large surface area in contact with a user's skin, have buckles that contact and cause discomfort with a user's skin, or are generally more bulky. Each of these aspects of previous configurations is undesirable, especially when used in athletic competitions. It would be desirable to provide a tendon strap that would not lose tension, would be comfortable against a user's skin, and would not be bulky when worn.

SUMMARY

The present invention can include a tendon supporting band and method where a tubular member provides therapeutic effect to a tendon of a user so that the tendon supporting band does not lose tension, is comfortable to wear, and is minimally bulky. The tendon supporting band can include at least one elongated flexible tubular member and at least one buckle. Each tubular member can have a first end, a second end, and a predetermined length sufficient to completely encircle a joint of a user at a point immediately adjacent to the joint with enough additional length that the second end can be adjustably threaded through the buckle and reversibly folded over a central portion of the tubular member. Having both the tendon supporting portion and the securing portion of the band formed of a single unitary tubular member allows the band to avoid having to connect different types of material together that could cause structural weakness in the band, add unnecessary bulk, or otherwise be uncomfortable when contacting the skin. The first end of the tubular member can be connected with a buckle for adjustably receiving the second end of the tubular member in an interlocking relationship to secure the tendon strap to the joint. The flexible characteristic of the tubular member allows the band to conform for use on multiple different joints and different body sizes. The buckle allows for adjustable tension control. The act of reversibly folding the second end of the tubular member through the buckle, in combination with a sufficiently high coefficient of friction of the tubular member, allows the tendon supporting band to avoid losing tension throughout prolonged vigorous activity. Additionally, the physical characteristics of the tendon supporting band in combination with the rigidity of the tubular member allow the tubular member to support the buckle away from contacting the user's skin.

A tendon strap for engaging with respect to a joint of a user can include at least one elongated flexible tubular member with a first end and a second end. The tubular member can have a predetermined length sufficient to completely encircle a joint of the user at a point immediately adjacent to the joint with sufficient additional length to allow for adjustment. A buckle can be connected adjacent to the first end of the tubular member and can adjustably receive the second end of the tubular member in interlocking relationship to secure the tendon strap to the joint of the user.

The first end of the tubular member can be connected with the buckle for adjustably receiving the second end of the tubular member in an interlocking relationship to secure the tendon strap to the joint. The first end of the tubular member can be secured to the buckle using a fastener by inserting the first end through the buckle, reversibly folding over the tubular member encircling the buckle, and fixedly securing the tubular member and buckle with respect to one another. Fixedly securing the buckle to one end of the tubular member has the advantage of making the band easier to use, as only one end of the band needs to be adjustable in order to carry out its intended use. At least one securing member can be used to secure the second end after the second end is inserted through the buckle and reversibly folded over the tubular member, encircling the buckle, thus adjustably securing the tubular member and buckle with respect to one another. The buckle can define at least one aperture. The at least one aperture of the buckle can be at least as large as a largest dimension of the tubular member when in a radially compressed state. The tubular member and the buckle can be formed with dimensions allowing the buckle to be suspended by the tubular member away from an inside periphery of the tendon strap when formed as a loop around the joint of the user in order to assist in preventing contact of the buckle with skin of the user while being worn by the user.

A method of producing a tendon strap can include the steps of providing an elongated flexible tubular member of a predetermined length having a first end and a second end, providing a buckle with dimensions allowing passage of the tubular member therethrough, and securing the buckle to the tubular member adjacent to the first end. The method, if desired, can further include one or more of the following steps: inserting the first end of the tubular member through the buckle, reversibly folding the first end of the tubular member over a central portion of the tubular member after passing through the buckle, securing the first end to the tubular member with a fastener, covering the first end and fastener with a flexible sleeve, inserting the second end of the tubular member through the buckle, reversibly folding the second end of the tubular member over the central portion of the tubular member to encircle the buckle, and adjustably securing the second end of the tubular member with respect to the buckle with at least one securing member.

The tendon supporting band can be universally applied to a plurality of different joints on a body of the user. Also, the tendon supporting band can have a therapeutic effect with a minimal amount of components thereby minimizing bulk, as well as being inherently minimally expensive to manufacture. Lastly, the tendon supporting band can have the ability to be manufactured in a variety of different colors adding to an aesthetic appeal and desirability of the band.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views. Further aspects and advantages of the tendon supporting band will become apparent given the following illustrative embodiments of the band, and wherein.

DETAILED DESCRIPTION

Figure 1:
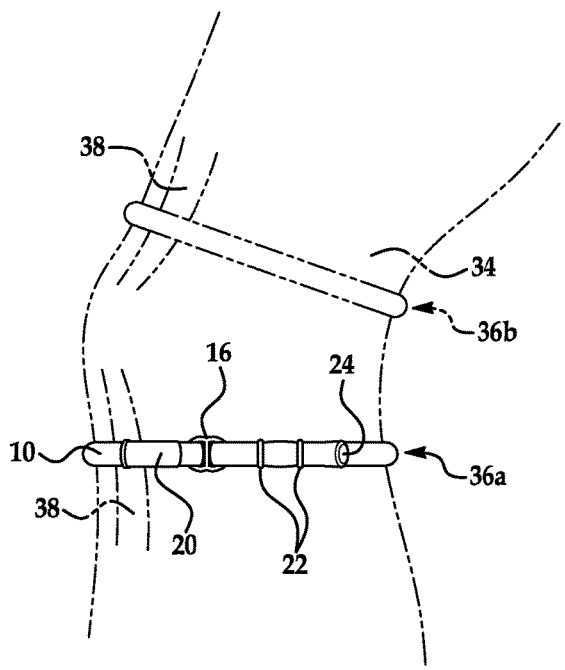
FIG. 1 is a front view of a typical joint of a user in phantom lines, illustrating a potential position for a tendon supporting band use on one side of the joint as shown in solid lines, or on an opposite side of the joint as shown in phantom, the tendon supporting band having at least one tubular member.
Figure 5:
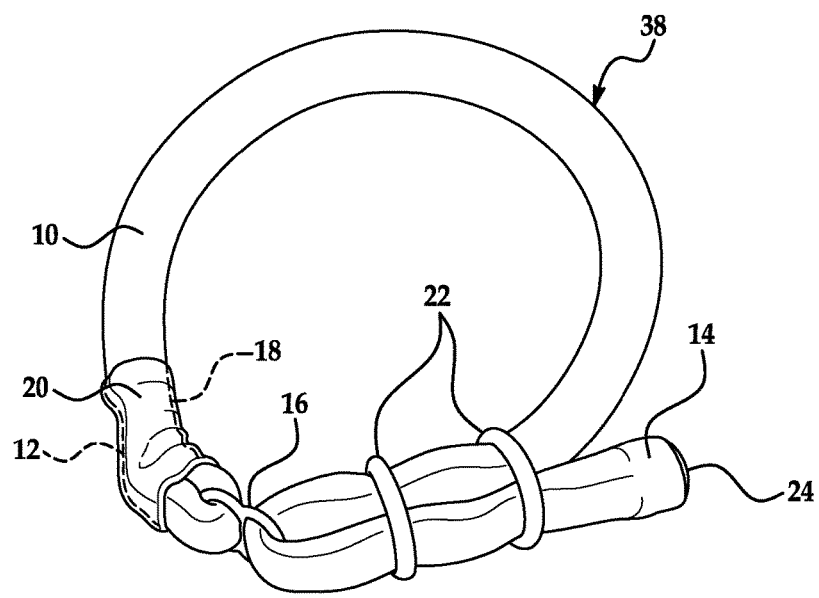
FIG. 5 is a plan view of the tendon supporting band.

A tendon supporting band 36a, 36b can be configured to be secured adjacent to a joint 34 of a user and has been optimized for use during athletic competition. The tendon supporting band can be worn on either side of the joint, above (as shown in phantom line at 36b in FIG. 1) or below (as shown in solid line at 36a in FIG. 1) the joint 34, or in close proximity to the joint 34. FIGS. 1 and 5 illustrate the tendon supporting band as an assembly configured in a fashion to be worn by a user. By way of example and not limitation, the joint of the user can include at least one of an elbow, a knee, an ankle, and a wrist.

Figure 2:
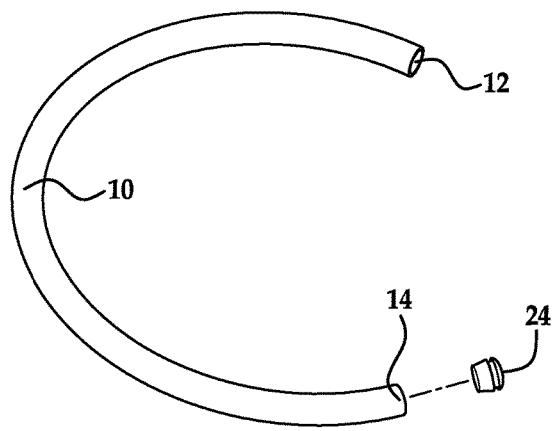
FIG. 2 is an exploded view of the tubular member including an end cap connected to a second end of the tubular member.
Figure 3:
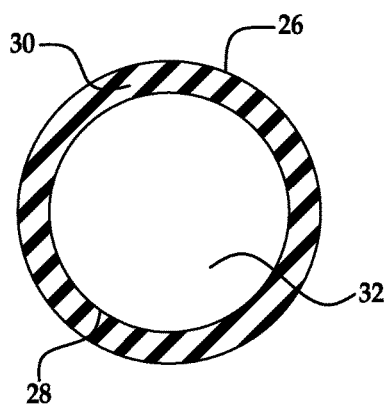
FIG. 3 is a cross sectional view of the tubular member of FIG. 1.

Referring to FIG. 5, an assembled tendon band is depicted as worn by a user. By way of example and not limitation, the illustrated configuration includes one elongated flexible tubular member 10, also shown in FIG. 2. This embodiment includes a buckle 16 with two apertures. Each aperture of the buckle 16 can be slightly larger than the cross sectional circumference of the compressed tubular member. The buckle 16 is sufficiently thin so that the circumference and rigidity of the tubular member will cause the buckle to be suspended off of the adjacent skin of the user when in use, aiding comfort and alleviating the need for additional underlying material to shield the skin of the user from contact with the buckle 16.

Figure 4:
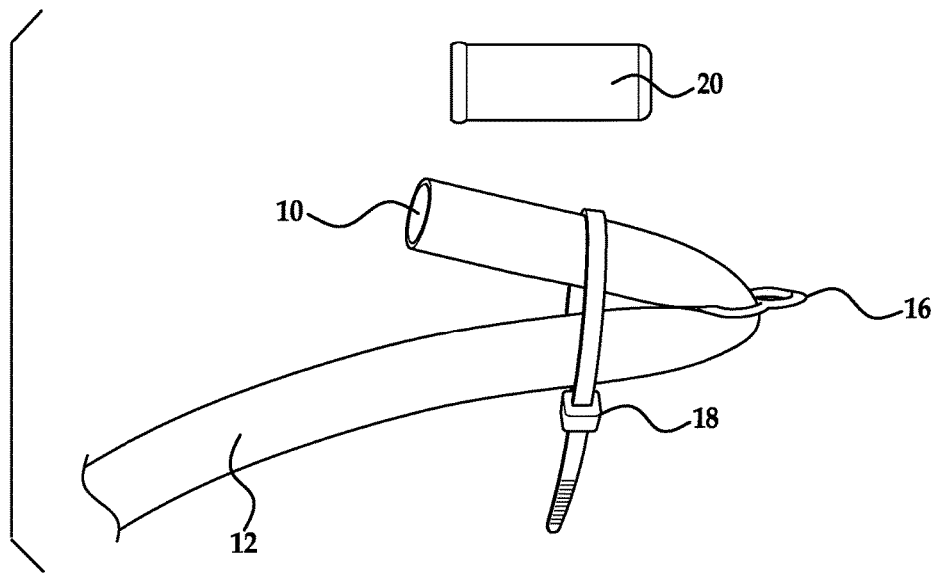
FIG. 4 is an exploded view of a first end of the tubular member shown in FIG. 1 having a fastener to secure a buckle to the tubular member and a rubber sleeve to cover the fastener and the first end of the tubular member.

Turning now to FIGS. 4 and 5, the tendon supporting band includes a fastener 18 for fixedly securing the buckle 16 to the tubular member 10 near the first end 12. The fastener 18 fixedly secures the first end 12 of the tubular member 10 to another area of the tubular member 10 after being reversibly folded over the buckle 16. The fastener 18 attaches an area or portion of the tubular member 10 immediately adjacent to the first end 12 to an area of the tubular member 10 slightly before the tubular member 10 threads through the buckle 16. By way of example and not limitation, FIGS. 4 and 5 show a flexible sleeve 20 covering the first end 12 of the tubular member 10 and the fastener 18. The flexible sleeve 20 can be made of a soft material and can prevent the rigid fastener 18 from coming into contact with the skin of the user. The flexible sleeve 20 can also aid in fixedly securing the buckle 16 by applying compressive force to the first end 12 and the tubular member 10 reducing the likelihood that the first end 12 will slip out of the fastener 18 and disengage the buckle 16.

Referring to FIGS. 1 and 5, the second end 14 of the tubular member 10 threads though the buckle 16 to adjustably secure the tendon supporting band to the joint of the user. After the second end 14 threads through the buckle 16, an additional amount of the tubular member 10 can also be threaded through. Threading more of the tubular member 10 through the buckle 16 can accomplish two different things. First, the greater a length of the tubular member 10 threaded through the buckle 16 results in a smaller circumference of the tendon supporting strap. The circumferential adjustment allows a user to adjust the inside diameter of the tendon supporting band to fit the joint of the user requiring therapeutic treatment. Secondly, once the tendon supporting band 36a, 36b is placed in the desired location and fit to the joint 34, an additional length of the tubular member 10 can be threaded through the buckle 16 in order to increase the amount of tension applied on the tendon 38 associated with the joint 34. This is accomplished because as the length of the flexible tubular member 10 is reduced, the tubular member 10 will stretch and apply more pressure to the joint given the constant diameter of the joint if the user.

The tendon supporting band can also include at least one securing member 22 for adjustably securing the buckle 16 to the tubular member 10 near the second end 14. The securing member 22 adjustably secures the second end 14 of the tubular member 10 to another more central area of the tubular member 10 after the second end 14 is reversibly folded over the buckle 16. The securing member 22 also aids in securing the tendon band to the joint of the user by preventing the second end 14 of the tubular member 10 from threading back through the buckle 16.

By way of example but not limitation, FIGS. 1 and 5 show two securing members 22 used to secure the second end 14 to the tubular member 10 after the second end 14 is threaded through the buckle 16. One securing member 22 is attached to the area adjacent to the second end 14 immediately before the tubular member 10 is threaded through the buckle 16 in the vicinity of an area immediately after the tubular member 10 exits the buckle 16. This first securing member 22 allows the tubular member 10 to adjustably secure the buckle 16 and prevents the tendon band from losing tension during use. FIGS. 1 and 5 also show the use of a second securing member 22. This second securing member 22 is attached to an area of the tubular member 10 immediately adjacent to the second end 14 in an area of the tubular band farther away from where the second end 14 is threaded though the buckle 16 than the first securing member 22. The second securing member 22 in this embodiment is primarily used to secure the second end 14 and the excess length of the tubular member 10 threaded through the buckle 16, so that the excess length of the tubular member 10 is not free to move while the tendon band is in use. Additionally, the second securing member 22 can also aid in preventing the tubular member 10 adjacent to the second end 14 from threading back through the buckle 16 causing the tendon band from losing tension.

An end cap 24 can be provided for terminating the second end 14 of the tubular member 10. The end cap 24 can have a collar of smaller diameter extending from an enlarged flange portion such that when the collar is inserted into the second end 14 of the tubular member 10, an elastic wall of the tubular member 10 constricts around the collar and holds the end cap 24 in place. The end cap can be provided for primarily aesthetic purposes to provide a finished appearance to the tendon supporting strap.

The flexible tubular member 10 is capable of being secured to any joint of a user provided the exterior of the joint is a peripheral length less than an overall maximum peripheral length of the tubular member 10 prior to tightening. The tendon supporting band can be used in a therapeutic manner by applying compressive pressure to tendons immediately adjacent to a joint. The compressive pressure can have a plurality of therapeutic affects including, but not limited to, adjusting the tendon into proper alignment and alleviating discomfort associated with the use of a joint.

In addition to therapeutic effects, tendon supporting bands and other corrective devices, especially in athletic settings, can be worn solely for aesthetic purposes. The minimally bulky nature of this invention in combination with the comfortable materials, make it ideally suited for this purpose.

A method for manufacturing the tendon supporting band can include the following steps. A flexible tubular member 10 of sufficient length is provided to fully encircle a target joint of a user with sufficient additional length to allow for the second end 14 of the tubular member 10 to be threaded through the buckle 16 and reversibly folded over the tubular member 10. A buckle 16 can be provided with suitable dimensions to allow insertion of the tubular member therethrough. The buckle 16 can have two apertures, where each aperture has a rectangular periphery with one inside dimension smaller than an outside diameter of the uncompressed tubular member 10 and another dimension larger than the outside diameter of the compressed tubular member 10. The buckle 16 can be sufficiently thin to avoid contact with skin of the user, while being formed of structural material thick enough to be stable under any intended conditions of use. The buckle 16 can be fixedly secured to the tubular member 10 adjacent to the first end 12.

By way of example but not limitation, the buckle 16 can be attached to the tubular member 10 by inserting the first end 12 of the tubular member 10 through the buckle 16, reversibly folding the first end 12 over the tubular member 10 after passing the first end 12 of the tubular member 10 though the buckle 16. The first end 12 of the tubular member 10 can be fixedly secured to the tubular member 10 using a suitable fastener 18. The first end 12 of the tubular member 10 and the fastener 18 can be covered using a flexible sleeve 20. At least one securing member 22 can be provided if desired for securing the second end 14 to the tubular member 10 after being adjustably threaded thorough the buckle 16.

By way of example and not limitation, suitable materials for the tubular member 10 can include a cylindrical latex surgical tubing having a cylindrical wall 30 having an outside diameter 26 between approximately $1\frac{1}{8}$" and approximately $\frac{1}{8}$" inclusive, an internal cavity 32 with an inside diameter 28 between approximately $\frac{15}{16}$" and approximately $\frac{1}{16}$" inclusive, and a wall thickness between approximately $\frac{3}{16}$" and approximately $\frac{1}{64}$" inclusive; and more preferably with an outside diameter 26 between approximately $\frac{5}{8}$" and approximately $\frac{3}{16}$" inclusive, an internal cavity 32 with an inside diameter 28 between approximately $\frac{1}{2}$" and approximately $\frac{1}{8}$" inclusive, and a wall thickness between approximately $\frac{1}{8}$" and approximately $\frac{1}{32}$" inclusive; and most preferably with an outside diameter of approximately $\frac{3}{8}$", an internal cavity with an inside diameter of approximately $\frac{1}{4}$", and a wall thickness of approximately $\frac{1}{16}$". By way of example and not limitation, a suitable cylindrical latex surgical tubing is available commercially from The Hygenic Corporation company located in Akron, Ohio and identified for sale under the trade name TheraBand® Exercise Tubing or product number #21150.

While the invention and method have been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A tendon strap for engaging with respect to a joint of a user comprising:
   at least one elongated flexible tubular member with a first end, a second end, and a central portion, each tubular member having a constant uniform cross section along an entire length between the first end and the second end when uncompressed, each tubular member having a predetermined length between the first end and the second end sufficient to completely encircle the joint of the user at a point immediately adjacent to the joint with sufficient additional length to allow for adjustment around the joint while each tubular member compresses the joint;
   a buckle connected adjacent to the first end of the tubular member and adjustably receiving the second end of the tubular member in interlocking relationship to secure the tubular member to the joint; and
   said second end reversibly folded over the central portion;
   wherein the reversibly folded second end of the tubular member is secured to a portion of the tubular member;
   wherein the joint is selected from the group consisting of an elbow, a knee, an ankle, and a wrist.

2. The tendon strap of claim 1 further comprising: a fastener for securing the tubular member to the buckle with the first end inserted through the buckle, reversibly folded over the tubular member encircling the buckle, the fastener fixedly securing the tubular member and buckle with respect to one another.

3. The tendon strap of claim 1 further comprising a flexible sleeve covering a fastener and first end of the tubular member.

4. The tendon strap of claim 1, wherein the tubular member and the buckle are formed of dimensions allowing the buckle to be suspended by the tubular member away from the inside periphery of the tendon strap when formed as a loop around a joint of the user in order to assist in preventing contact of the buckle with the skin of the user while being worn by the user.

5. The tendon strap of claim 1 further comprising the second end when reversibly folded with respect to the buckle secured to the tubular member with at least one securing member.

6. A tendon strap for engaging with respect to a joint of a user comprising:
   a single elongated flexible tubular member with a first end, a second end, and a central portion, the tubular member having a length between the first end and the second end to completely encircle the joint of the user at a point immediately adjacent to the joint with sufficient additional length to allow for adjustment around the joint while the tubular member compresses the joint, the tubular member having a constant uniform cross section along an entire length between the first end and the second end when uncompressed;
   a buckle connected adjacent the first end of the tubular member for adjustably receiving the second end of the tubular member in interlocking relationship to secure the tendon strap to the joint;
   a fastener for securing the tubular member to the buckle with the first end inserted through the buckle, reversibly folded over the tubular member encircling the buckle, the fastener fixedly securing the central portion; and
   at least one securing member securing the second end after being inserted through the buckle and reversibly folded over the central portion, the securing member adjustably securing the tubular member and buckle with respect to one another;
   wherein the joint is selected from the group consisting of an elbow, a knee, an ankle, and a wrist.

7. The tendon strap of claim of 6 further comprising: a flexible sleeve covering the fastener and first end of the tubular member.

8. The tendon strap of claim 6, wherein the buckle defines at least one aperture and at least one aperture is at least as large as a largest dimension of the tubular member when in a compressed state.

9. The tendon strap from claim 6, wherein the tubular member is made from a material with a coefficient of friction, such that when the tubular member is compressed and looped through the buckle, the coefficient of friction is sufficiently high to assist in preventing the tubular member from losing tension during use.

10. The tendon strap of claim 6, wherein the tubular member and the buckle are formed of dimensions allowing the buckle to be suspended by the tubular member away from an inside periphery of the tendon strap when formed as a loop around a joint of the user in order to assist in preventing contact of the buckle with skin of the user while being worn by the user.

11. The tendon strap of claim 6, wherein the securing member is movable with respect to both the tubular member and the second end.

12. The tendon strap of claim 6, wherein the securing member is affixed to the tubular member adapted to removably attach to the second end.

13. The tendon strap of claim 6, wherein the securing member is affixed to the second end adapted to removably attach the tubular member.

14. A method of securing a tendon strap to a user, comprising:
   providing an elongated flexible tubular member of a predetermined length having a first end and a second end;
   providing a buckle with dimensions allowing passage of the tubular member therethrough;
   inserting the first end of the tubular member through the buckle;
   reversibly folding the first end of the tubular member over a central portion of the tubular member after passing through the buckle;
   securing the first end to the tubular member with a fastener;
   covering the first end and fastener with a flexible sleeve;
   wrapping the tubular member around a user adjacent to a joint, the joint being selected from the group consisting of an elbow, a knee, an ankle, and a wrist;
   inserting the second end of the tubular member through the buckle;
   reversibly folding the second end of the tubular member over the central portion of the tubular member to encircle the buckle; and
   adjustably securing the second end of the tubular member with respect to the buckle with at least one securing member.

15. A tendon strap for engaging with respect to a joint of a user comprising:
   at least one elongated flexible tubular member with a first end and a second end, each tubular member having a constant uniform cross section along an entire length between the first end and the second end when uncompressed, each tubular member having a predetermined length between the first end and the second end sufficient to completely encircle the joint of the user at a point immediately adjacent to the joint with sufficient additional length to allow for adjustment around the joint while each tubular member compresses the joint; and
   a buckle connected adjacent to the first end of the tubular member and adjustably receiving the second end of the tubular member in interlocking relationship to secure the tubular member to the joint; and
   a securing member which removably attaches to both the second end and the tubular member securing both the second end and the tubular member together;
   wherein the joint is selected from the group consisting of an elbow, a knee, an ankle, and a wrist.

16. The tendon strap of claim 15, wherein the securing member is movable with respect to both the tubular member and the second end.

17. The tendon strap of claim 15, wherein the securing member is affixed to the tubular member adapted to removably attach the second end.

18. The tendon strap of claim 15, wherein the securing member is affixed to the second end adapted to removably attach the tubular member.

* * * * *